United States Patent [19]

Shimizu et al.

[11] 4,422,735
[45] Dec. 27, 1983

[54] FUNDUS CAMERA

[75] Inventors: Tsutomu Shimizu, Hanno; Koji Inaba; Naomiki Araki, both of Hachioji, all of Japan

[73] Assignee: Olympus Optical Company, Ltd., Japan

[21] Appl. No.: 229,463

[22] Filed: Jan. 29, 1981

[30] Foreign Application Priority Data

Apr. 22, 1980 [JP] Japan .................................. 55-52385

[51] Int. Cl.³ .............................................. A61B 3/14
[52] U.S. Cl. ...................................... 351/206; 354/62
[58] Field of Search ..................... 351/7, 206; 350/52, 350/484; 354/62

[56] References Cited

U.S. PATENT DOCUMENTS 4,279,507 7/1981 Bulpitt ............................ 350/484 X

FOREIGN PATENT DOCUMENTS 53-26685  3/1977  Japan .
54-49025  4/1978  Japan .
146412   5/1921  United Kingdom ................ 350/52

Primary Examiner—F. L. Evans
Attorney, Agent, or Firm—Ostrolenk, Faber, Gerb & Soffen

[57] ABSTRACT

A fundus camera includes an objective lens which is movable in a plane perpendicular to the principal optical axis thereof. The camera also includes an optical system comprising four reflecting surfaces which move as the objective lens is moved to compensate for an optical path length, the arrangement being such that a visual axis of an eye being examined can be brought into alignment with the principal optical axis of the objective lens without changing the length of the observation and photographing light path, by means of a movement of only part of the optical system and without moving the entire main body.

8 Claims, 6 Drawing Figures

FUNDUS CAMERA

BACKGROUND OF THE INVENTION

The invention relates to a fundus camera, in particular, to such a camera which facilitates a relative positioning of the camera with respect to an eye being examined.

A conventional fundus camera includes two essential parts, a main body having an optical system and a rack which supports the main body. By changing the relative position between the main body and the rack, the visual axis of an eye being examined is brought into alignment with the principal optical axis of an objective. Referring to FIG. 1 for a description of a conventinal fundus camera, it includes a base 1 which is placed on a desk, for example. A carriage 2 is disposed on the base 1 so as to be movable in a horizontal plane in a fore-and-aft direction and also in a lateral direction. The carriage 2 is provided with an operating handle 3 which permits a movement of the carriage 2 in the horizontal plane. A main body 4 internally houses an optical system which includes an objective 4a located on the front end or on the left-hand end, as viewed in FIG. 1, and an eyepiece assembly 4b located on the rear end or on the right-hand side. A support shaft 5 depends downwardly from the bottom of the main body 4 and is fitted into a holding sleeve 6 which is fixedly mounted on the carriage 2, thus supporting the main body 4. An operating ring 7 is disposed around the upper end of the holding sleeve 6 in concentric relationship therewith for angular movement thereabout to change the degree of fitting engagement between the shaft 5 and the sleeve 6 through means such as a helicoid screw, not shown, thereby changing the vertical height of the main body 4 relative to the carriage 2. A support member 8 extends forwardly and upwardly from the front end of the base 1 and fixedly carries a chin receiver 9 on its top end.

FIG. 2 shows an optical system which may be disposed within the main body 4. Specifically, it includes an objective lens 12 located in opposing relationship with an eye 11 to be examined, an apertured reflecting mirror 13 located rearwardly of the objective lens 12 at an angle of 45° with respect to the principal optical axis of the lens 12, a relay lens 14 disposed further rearward of the apertured reflecting mirror 13, a light path switching mirror 16 rockably disposed between the relay lens 14 and a photographic film 15, a mirror 17 disposed above the switching mirror 16 to form an observation light path, and an eyepiece 18 disposed in opposing relationship with the mirror 17.

In the conventional fundus camera thus constructed, the visual axis of the eye 11 of the patient being examined who has his chin placed on the chin receiver 9, is brought into alignment with the principal optical axis of the objective lens 12 by suitably operating the handle 3 and the operating ring 7 to move the main body 4 in fore-and-aft and lateral directions as well as in the vertical direction while observing, from the lateral direction, the location and the degree of defocusing of an image of an annular slit (not shown), which is disposed in an illumination system, on the front portion of the eye 11. When the visual axis of the eye 11 is brought into alignment with the principal optical axis of the objective lens 12, illuminating light from a light source which has passed through the annular slit impinges from below in a direction indicated by arrow a, and is reflected by the apertured reflecting mirror 13 to pass through the objective lens 12 to illuminate the fundus oculi of the eye 11 being examined. Reflected light from the fundus oculi passes through the objective lens 12 and a central aperture 13a formed in the reflecting mirror 13 and is then successively reflected by the mirror 16 and the mirror 17 to reach the eye 19 of a viewer through the eyepiece 18. In this manner, the viewer is capable of observing an image of the fundus oculi of the eye 11. Under the condition that a good image of the fundus oculi is observed, the switching mirror 16 may be turned in a direction indicated by arrow b until the phantom line position is reached where it is located out of the principal optical axis, whereupon the image of the fundus oculi of the eye 11 is focused onto the photosensitive surface of the film 15, permitting a picture thereof to be taken.

However, it will be appreciated from the foregoing description that with the conventional fundus camera, the entire main body 4 must be moved in order to bring the visual axis of the eye 11 into alignment with the principal optical axis of the objective lens 12, thus disadvantageously requiring a large and complex moving mechanism.

In addition, each time the main body 4 is moved, the location of the viewer's eye must be changed, causing inconvenience in the operation of the arrangement.

SUMMARY OF THE INVENTION

It is an object of the invention to provide a fundus camera which permits the visual axis of an eye being examined to be brought into alignment with the principal optical axis of an objective lens by simply moving part of the optical system.

In accordance with the invention, it is unnecessary to move the entire main body for achieving the alignment. Rather, only part of the optical system need be moved, thus dispensing with an elaborate moving mechanism.

In addition, the viewer's eye may be maintained at a fixed location during the alignment operation, greatly facilitating the operation of the apparatus.

BRIEF DESCRIPTION OF TH DRAWINGS

DESCRIPTION OF THE PREFERRED EMBODIMENTS

Figure 1:
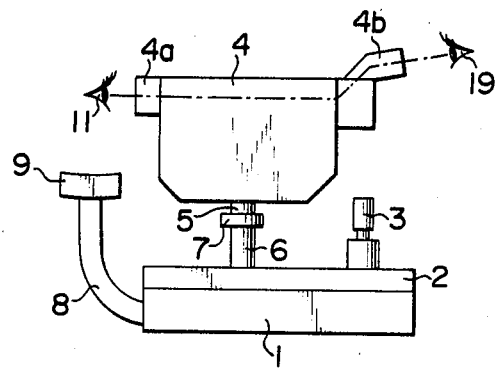
FIG. 1 is a schematic side elevation of one examplary fundus camera of the prior art.
Figure 2:
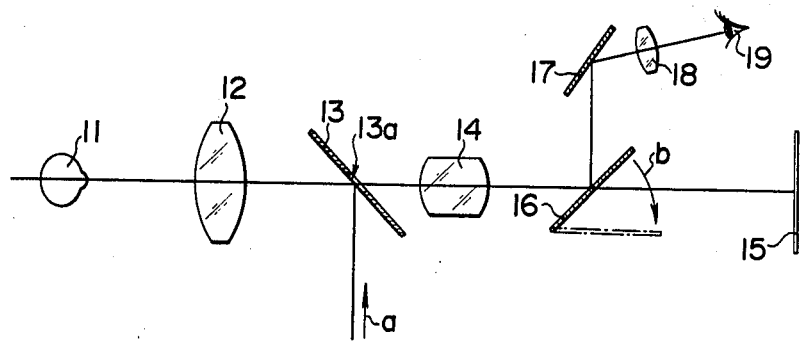
FIG. 2 is a schematic diagram of one form of an optical system which is used in the camera of FIG. 1.
Figure 3:
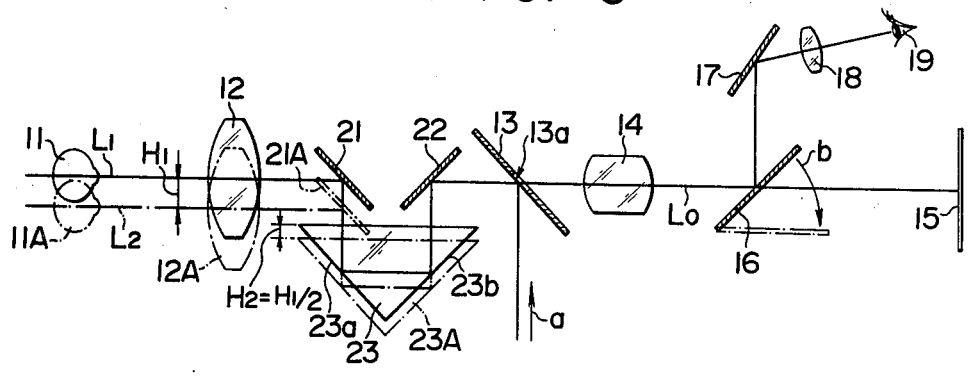
FIG. 3 is a schematic diagram of the optical system of a fundus camera according to one embodiment of the invention.

Referring to FIG. 3, there is shown the optical system of a fundus camera according to one embodiment of the invention. This optical system differs from that shown in FIG. 2 in that a pair of light path changing reflecting mirrors 21, 22 and a right-angle prism 23, which compensates for the optical path length, are interposed between the objective lens 12 and the apertured reflecting mirror 13, and in that the objective lens 12 is disposed to be movable in a plane which is perpendicular to the principal optical axis thereof.

One of the path changing mirrors, 21, is located in opposing relationship with the objective lens 12 at an angle of 45° with respect to the principal optical axis of the latter, and serves to change the optical path of illuminating light and/or observation or photographing light which passes through the objective lens 12 on a path that is perpendicular thereto. It is to be noted that the mirror 21 moves in the same direction and the same distance as the objective lens 12 moves. The other changing mirror 22 is disposed in opposing relationship with the apertured reflecting mirror 13 at an angle of 45° with respect to an observation and taking optical axis $L_O$ which passes through the center of the aperture 13a formed in the reflecting mirror 13, thus serving to divert the direction of the illuminating light as well as observation or photographing light through 90°.

The right-angle prism 23 is located below the path changing mirrors 21, 22 so that its face which faces the mutually right-angled edges is located horizontally in opposing relationship with mirrors 21, 22. The prism 23 is adapted, as the objective lens 12 moves, to move in the same direction as the latter through one-half distance travelled by the lens 12.

Other components of the optical system remain the same as those shown in FIG. 2, and hence corresponding parts are designated by like reference characters without repeating their description.

In the fundus camera of the invention in which the optical system shown in FIG. 3 is incorporated, the visual axis of the eye 11 can be brought into alignment with the principal optical axis of the objective lens 12 by causing the objective lens 12 to move in a plane which is perpendicular to the principal optical axis thereof and simultaneously moving the mirror 21 and prism 23. By way of example, assume that the eye 11 has its visual axis located on a phantom line position 11A which is displaced by a distance $H_1$ downward from a reference position shown in solid line where it is aligned with the observation and taking optical axis $L_O$. In this instance, the objective lens 12 is moved downward through a distance $H_1$ so that its principal optical axis is aligned with the visual axis of the eye 11 being examined. Thereupon, in interlocked relationship with the movement of the objective lens 12, the mirror 21 and the prism 23 move downward by distances of $H_1$ and $H_2 = \frac{1}{2}H_1$, respectively, assuming phantom line positions 21A, 23A, respectively. As a result, the illuminating light which is reflected by the apertured reflecting mirror 13 passes through the optical path $L_2$ shown in phantom line to be incident on the eye 11 being examined. The observation or photographing light which is reflected by the fundus oculi of the eye 11 reversely follows the optical path $L_2$ to reach the apertured reflecting mirror 13. More specifically, the observation and photographing light passes through the objective lens 12 and is then successively reflected by the mirror 21, the reflecting surfaces 23a, 23b of the prism 23 and the mirror 22 to reach the apertured reflecting mirror 13. Consequently, such light is allowed to pass through the central aperture 13a formed in the reflecting mirror 13 to permit an observation and taking a picture of the image of the fundus oculi of the eye 11 being examined, in the same manner as achieved with the conventional fundus camera shown in FIG. 2.

Since a reduction in the path length which is caused by the movement of the mirror 21 through the distance $H_1$ is compensated for an increase in the path length which is produced by the movement of the prism 23 through the distance $H_2 = \frac{1}{2}H_1$, the path length of the optical path $L_2$ remains unchanged from the length of the optical path $L_1$ which passes through the principal optical axis of the objective lens 12 in its reference position. Thus, there is no change in the path length before and after the movement of the objective lens 12, eliminating any adverse influence of the movement of the lens 12 upon the observation and the photographing operation.

Figure 4:
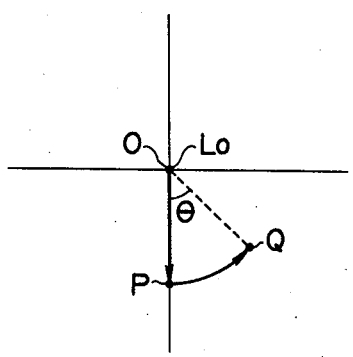
FIG. 4 is a schematic view illustrating the procedure of moving the principal optical axis of the objective lens of the fundus camera shown in FIG. 3.

In the described optical system, the objective lens 12, the mirrors 21, 22 and the prism 23 are arranged to be integrally rotatable about the observation and taking optical path $L_O$. Hence, if the objective lens 12 is rotated while it assumes the phantom line position shown in FIG. 3, the principal optical axis of the lens 12 rotates about the optical axis $L_O$. By a combination of such rotational movement and the movement in the radial direction mentioned above, it is possible to shift the principal optical axis of the objective lens 12 freely to any location where it passes through a desired point in the plane which is perpendicular to the axis. By way of example, assuming that the principal optical axis of the objective lens 12 passes through a point O shown in FIG. 4 when the lens assumes its reference position, it may be shifted to a point Q which is located to the right thereof and obliquely downward, by initially moving the objective lens 12 downward until the optical axis is aligned with a point P, followed by rotating the objective lens 12 counter-clockwise through an angle ← about the optical axis $L_O$. In this manner, the principal optical axis of the objective lens 12 can be brought to any point located within its extent of movement through a combination of the radial movement and the rotation about the optical axis $L_O$ of the objective lens 12.

Figure 5:
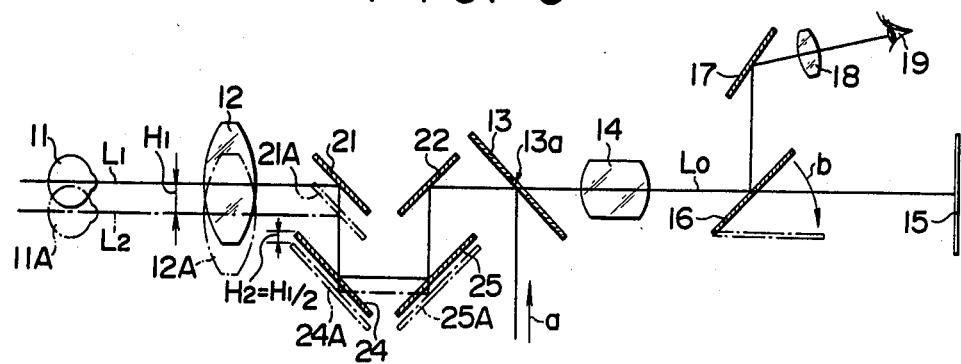
FIG. 5 is a schematic diagram of the optical system of a fundus camera according to another embodiment of the invention.

FIG. 5 shows the optical system of a fundus camera according to another embodiment of the invention. In this optical system, the path length compensating right-angle prism 23 shown in FIG. 3 is replaced by a pair of path length compensating total reflection mirrors 24, 25 which are disposed at right angles to each other. These total reflection mirrors 24, 25 moves, as the objective lens 12 moves, in the same direction as the latter and by one-half the distance travelled by the objective lens 12, in the same manner as the right-angle prism 23 moves.

Other components in this optical system correspond to those illustrated in FIG. 3, and hence corresponding parts are designated by like reference characters without repeating their description.

With a fundus camera which employs the optical system of this embodiment, as the objective lens 12 moves through a distance $H_1$ radially of the observation and photographing optical axis $L_O$, the mirror 21 moves through a distance $H_1$ and the mirrors 24, 25 move through a distance $\frac{1}{2}H^1$ in the same direction, and thus are displaced to their phantom line positions 21A, 24A, 25A, respectively. Consequently, there is no change in the length of the optical path of the observation and photographing light as a result such movement, avoiding any influence upon the observation and photographing operation.

Figure 6:
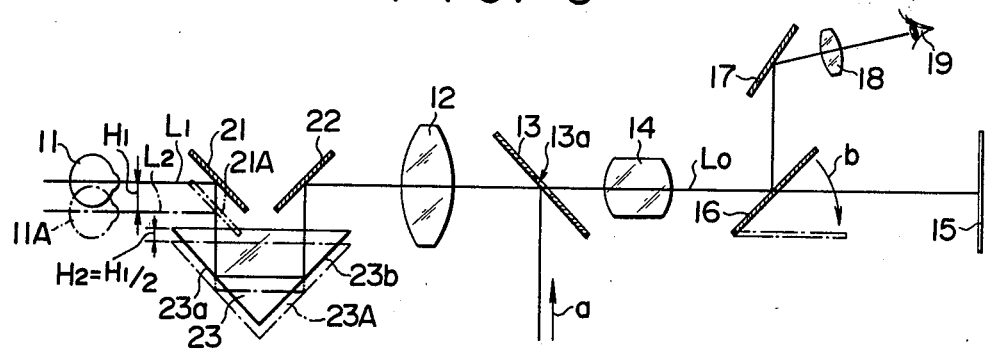
FIG. 6 is a schematic diagram of the optical system of a fundus camera according to a further embodiment of the invention.

FIG. 6 shows the optical system of a fundus camera according to a further embodiment of the invention. In this optical system, the right-angle prism 23 shown in FIG. 3 is disposed forwardly of the objective lens 12 rather than between the objective lens 12 and the apertured reflective mirror 13. In this optical system, the objective lens 12 is fixedly mounted in opposing relationship with the path changing mirror 22 while the right-angle prism 23 moves through one-half the distance travelled by the path changing mirror 21, which is located in opposing relationship with the eye 11 being examined, and in the same direction as the mirror 21.

With the fundus camera of the present embodiment incorporating the optical system thus constructed, the path length of the observation and photographing light does not change as a result the movement of the mirror 21 and the prism 23.

In the embodiments described above, the path changing mirrors 21, 22 have been constructed as total reflection mirrors, but may be replaced by the total reflecting surfaces of a prism.

What is claimed is:

1. A fundus camera, comprising:
    an objective lens having a principal optical axis;
    said objective lens being disposed to be movable in a plane which is perpendicular to said principal optical axis thereof to align said principal optical axis thereof with a visual axis of an eye being examined;
    a first reflecting surface disposed on the principal optical axis of said objective lens for movement simultaneously with and in the same direction and through the same distance as said objective lens;
    a second reflecting surface disposed for movement simultaneously with and in the same direction as and through one-half the distance travelled by said objective lens; said first reflecting surface reflecting light passing through said objective lens to said second reflecting surface;
    a third reflecting surface disposed for simultaneous movement with, and in the same direction as, said second reflecting surface and moving the same distance as said second reflecting surface, said second reflecting surface reflecting light reflected by said first reflecting surface to said third reflecting surface;
    a stationary fourth reflecting surface; said third reflecting surface reflecting light that has been reflected by said second reflecting surface to said fourth reflecting surface; and
    an apertured reflecting mirror disposed for reflecting illuminating light in a direction which will cause said illuminating light to be reflected by said fourth, third, second and first reflecting surfaces and through said objective lens to illuminate the fundus oculi of an eye being examined and which will also permit light reflected off the fundus oculi of the eye, and then passing through said objective lens and reflected off said first through fourth reflective surfaces, to pass through the aperture of said reflecting mirror so as to permit observation or photographing of the illuminated fundus oculi through said objective lens and through said aperture of said apertured mirror.

2. A fundus camera according to claim 1, further comprising means defining an observation and photographing optical path which passes through said aperture formed in said apertured mirror; said objective lens being rotatable, together with said first to fourth reflecting surfaces about said observation and photographing optical path.

3. A fundus camera according to claim 1, in which said first reflecting surface is disposed at an angle of 45° relative to said principal optical axis of said objective lens, said second reflecting surface is disposed in parallel opposing relationship to said first reflecting surface, said third reflecting surface is disposed perpendicular to said second reflecting surface, and said fourth reflecting surface is disposed in opposing relationship with said apertured mirror and parallel to said third reflecting surface.

4. A fundus camera, comprising:
    an objective lens having a principal optical axis;
    a first reflecting surface disposed for movement in a plane which is perpendicular to said principal optical axis of the objective lens to be brought into alignment with a visual axis of an eye being examined;
    a second reflecting surface disposed for movement simultaneously with, and in the same direction as and through one-half the distance travelled by, said first reflecting surface; said first reflecting surface reflecting light reflected off the fundus oculi of an eye being examined to said second reflecting surface;
    a third reflecting surface disposed for simultaneous movement with, and in the same direction as, said second reflecting surface and moving the same distance as said second reflecting surface, said second reflecting surface reflecting light that has been reflected by said first reflecting surface to said third reflecting surface;
    a stationary fourth reflecting surface; said third reflecting surface being disposed for reflecting light that has been reflected by said second reflecting surface to said fourth reflecting surface; said fourth reflecting surface being disposed for reflecting light reflected by said third reflecting surface through said objective lens; and
    an apertured reflecting mirror disposed on the principal optical axis of said objective lens for reflecting illuminating light in a direction which will cause said illuminating light to pass through said objective lens and to be reflected by said fourth, third, second and first reflecting surfaces to illuminate the fundus oculi of an eye being examined and which will also permit light reflected off the fundus oculi of the eye being examined, and then reflecting off said first to fourth reflecting surfaces and passing through said objective lens to pass through the aperture of said apertured mirror so as to permit observation or photographing of the illuminated fundus oculi through said objective lens and through said aperture of said apertured mirror.

5. A fundus camera according to claim 4, in which said first reflecting surface is disposed at an angle of 45° relative to a visual axis of an eye being examined, said second reflecting surface is disposed in parallel opposing relationship to said first reflecting surface, said third reflecting surface is disposed perpendicular to said second reflecting surface, and said fourth reflecting surface is disposed at an angle of 45° relative to said principal optical axis of said objective lens and parallel to said third reflecting surface.

6. A fundus camera according to claim 4, further comprising means defining an observation and photographing optical path which passes through said aperture formed in said apertured mirror; said objective lens being rotatable, together with said first to fourth reflecting surfaces about said observation and photographing optical path.

7. A fundus camera according to claim 1 or claim 4 in which said first, second, third and fourth reflecting surfaces each comprise a respective totally reflecting mirror surface.

8. A fundus camera according to claim 1 or claim 4 in which said second and third reflecting surfaces are respective totally reflecting surfaces formed on a single prism.

* * * * *